United States Patent
Fuss et al.

(10) Patent No.: US 6,599,294 B2
(45) Date of Patent: Jul. 29, 2003

(54) SURGICAL INSTRUMENT FOR INTRODUCING INTERVERTEBRAL IMPLANTS

(75) Inventors: Franz Konstantin Fuss, Wiener Neustadt (AT); Ronald J. Sabitzer, Vienna (AT); Stephan Eckhof, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/916,192

(22) Filed: Jul. 26, 2001

(65) Prior Publication Data

US 2002/0045904 A1 Apr. 18, 2002

Related U.S. Application Data

(63) Continuation of application No. PCT/EP00/00625, filed on Jan. 27, 2000.

(30) Foreign Application Priority Data

Jan. 30, 1999 (DE) .......................................... 199 03 762

(51) Int. Cl.[7] .............................................. A61B 17/66
(52) U.S. Cl. ........................ 606/99; 606/105; 600/201
(58) Field of Search .............................. 606/53, 61, 90, 606/99, 105; 600/201, 210, 217, 235, 219–222

(56) References Cited

U.S. PATENT DOCUMENTS

| | | | | |
|---|---|---|---|---|
| 3,744,481 A | * | 7/1973 | McDonald | .................. 600/213 |
| 4,356,821 A | * | 11/1982 | Rind | ...................... 128/207.14 |
| 4,697,586 A | * | 10/1987 | Gazale | ......................... 606/53 |
| 5,431,658 A | | 7/1995 | Moskovich | |
| 5,571,109 A | | 11/1996 | Bertagnoli | |
| 5,716,416 A | * | 2/1998 | Lin | ......................... 623/17.16 |
| 5,720,751 A | | 2/1998 | Jackson | |
| 5,885,300 A | | 3/1999 | Tokuhashi et al. | |
| 5,928,139 A | * | 7/1999 | Koros et al. | ................. 600/205 |
| 6,143,032 A | | 11/2000 | Schafer et al. | |

FOREIGN PATENT DOCUMENTS

| | | |
|---|---|---|
| DE | 43 28 690 | 3/1995 |
| DE | 197 13 416 | 10/1997 |
| DE | 297 20 022 | 1/1998 |
| DE | 299 01 611 | 4/1999 |
| EP | 0 641 547 | 3/1995 |

* cited by examiner

Primary Examiner—Kevin Shaver
Assistant Examiner—Michael B. Priddy
(74) Attorney, Agent, or Firm—Barry R. Lipsitz; Douglas M. McAllister

(57) ABSTRACT

In order, in the case of a surgical instrument for introducing intervertebral implants into the intervertebral space between adjacent vertebral bodies, to facilitate the introduction of the intervertebral implant even when access is difficult, it is proposed that the surgical instrument comprises two mutually opposing guide bodies, which each have a guide directed towards the other guide body and together form between them a guideway, along which an intervertebral implant is insertable laterally into the intervertebral space.

24 Claims, 8 Drawing Sheets

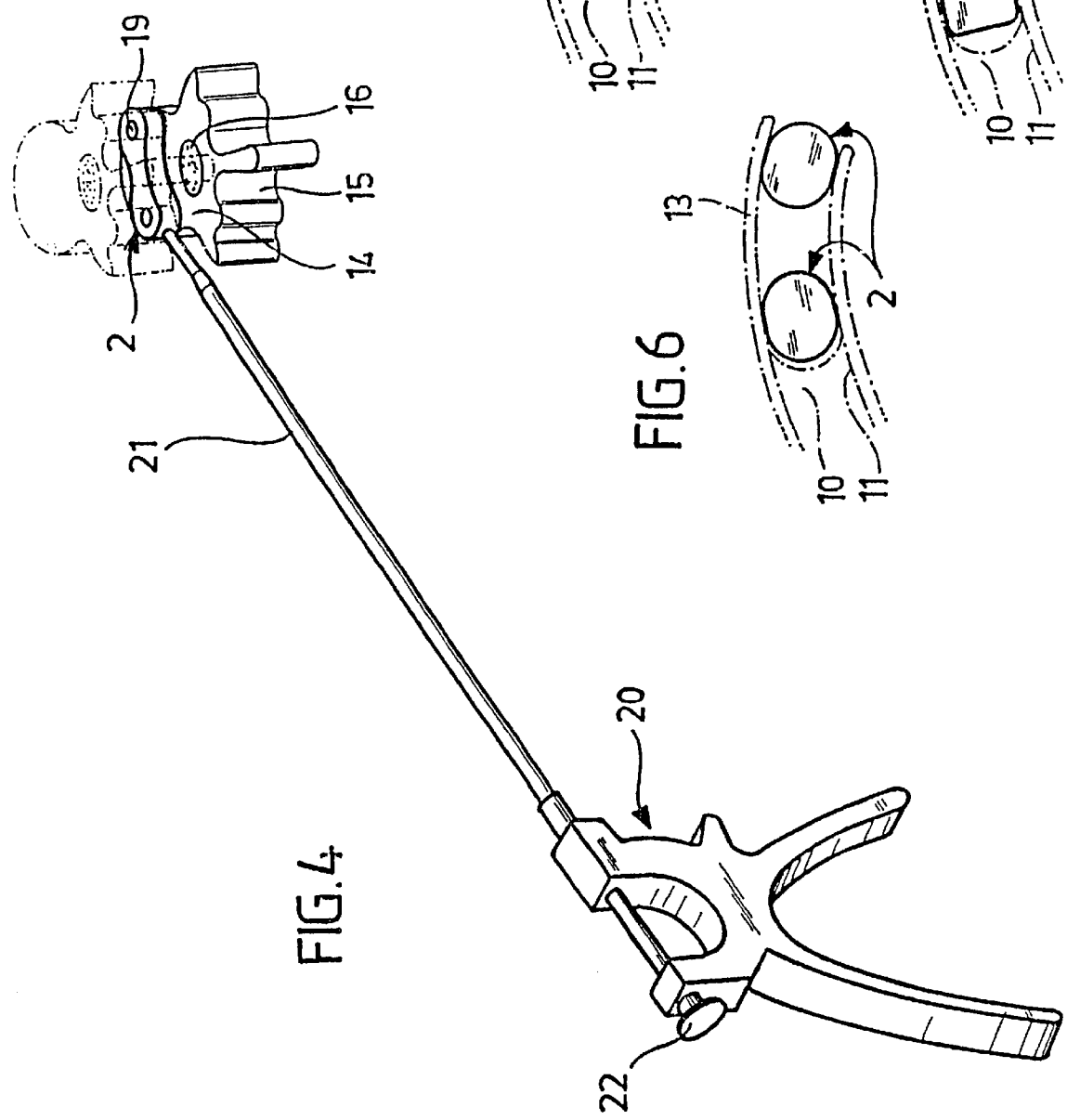

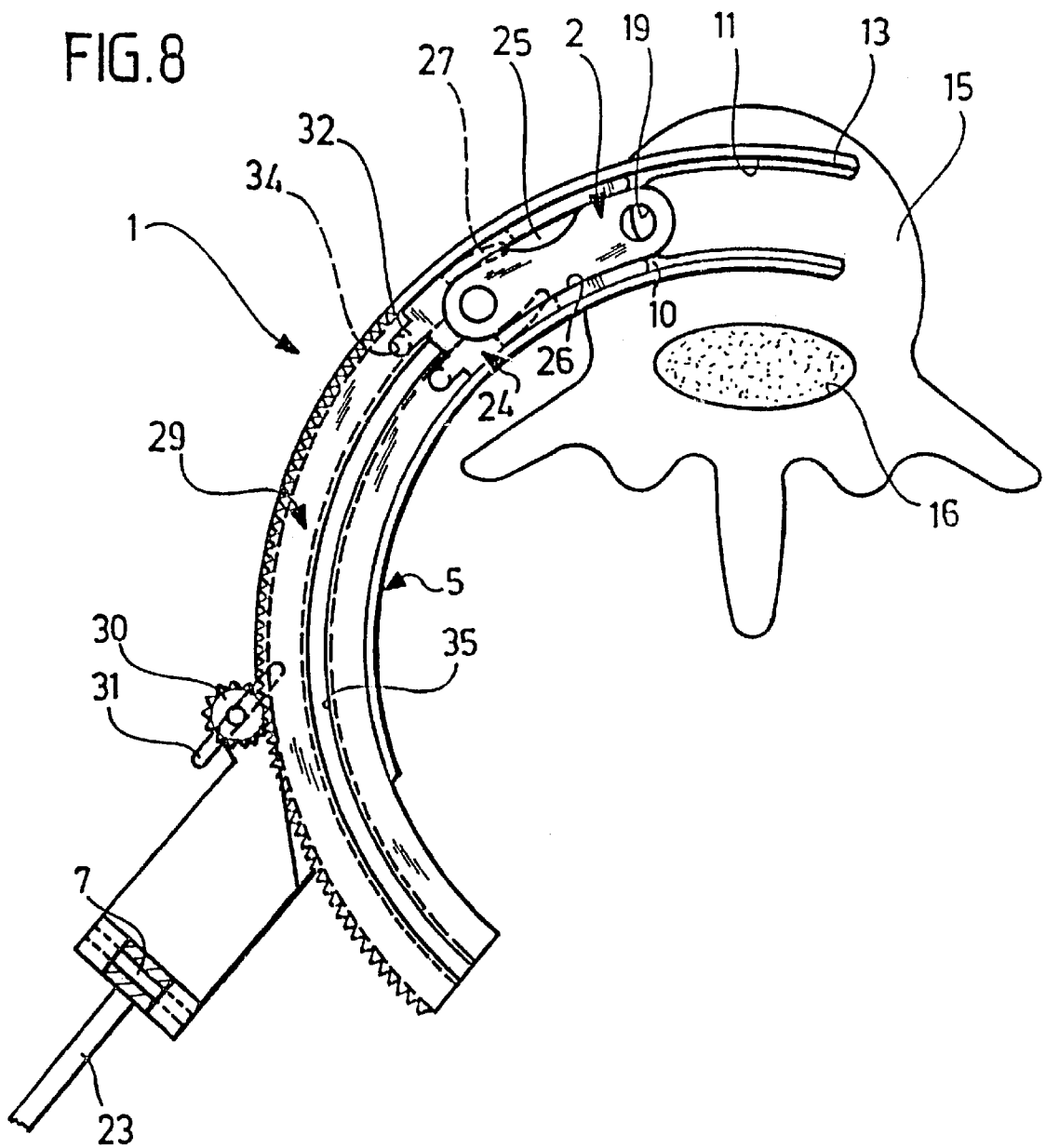

SURGICAL INSTRUMENT FOR INTRODUCING INTERVERTEBRAL IMPLANTS

Figure 1:
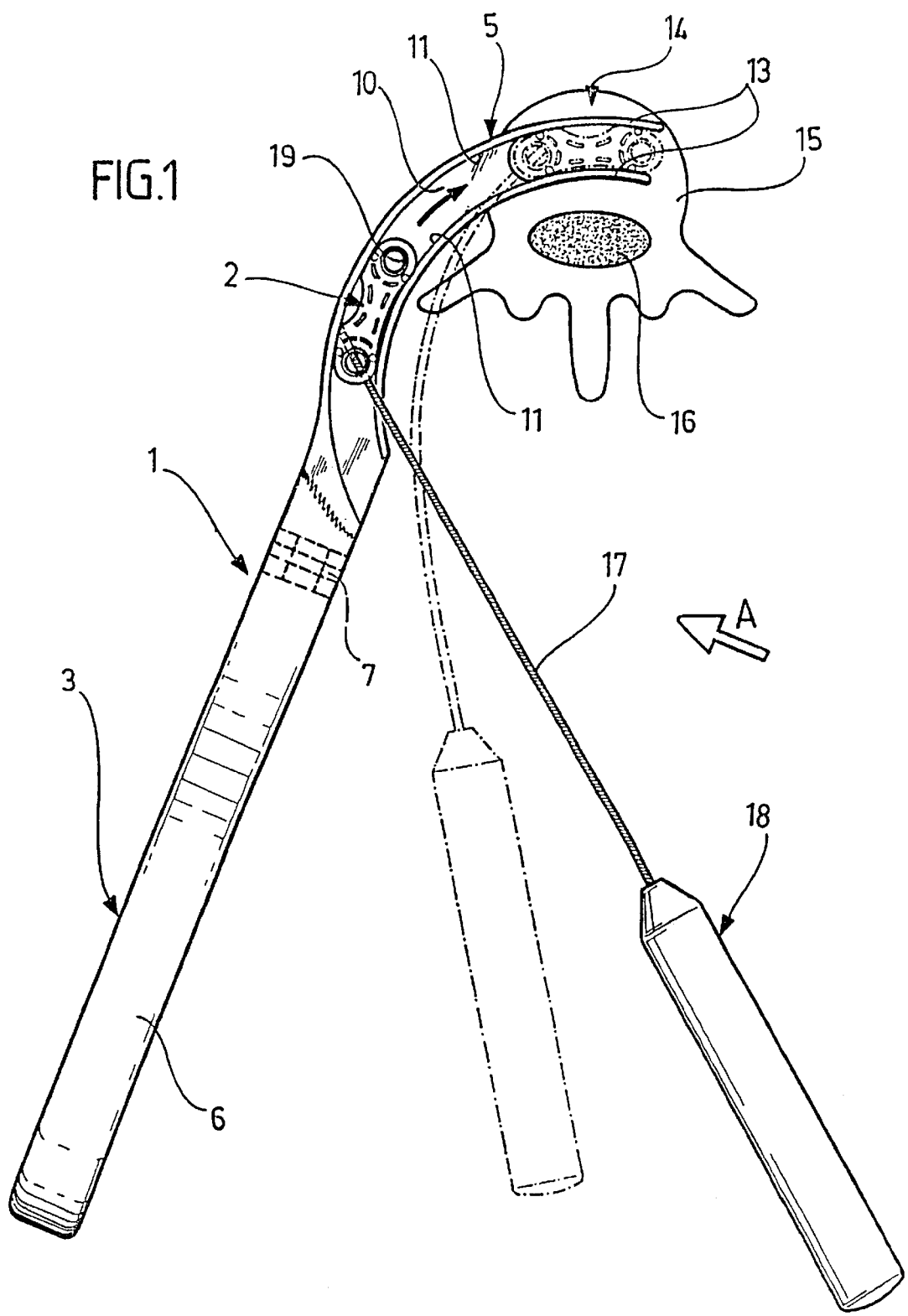

This application is a continuation of international application No. PCT/EP00/00625 filed on Jan. 27, 2000.

This application claims benefit of German Patent Application No. 199 03 762.0 filed Jan. 30, 1999.

The invention relates to a surgical instrument for introducing intervertebral implants into the intervertebral space between adjacent vertebral bodies.

Intervertebral implants are inserted in place of a removed disk into the intervertebral space between two adjacent vertebral bodies in order to maintain the distance between the latter and to enable the two adjacent vertebral bodies to stabilize through bone fusion after removal of the disk.

Introducing such an, as a rule, plate- or cage-shaped implant into the intervertebral space may be difficult because after removal of the disk the vertebral bodies are pressed towards one another by the action of the muscles. It is therefore necessary to use suitable stabilizing devices, e.g. bone plates with bone-screws, to fix the distance between the vertebral bodies.

Intervertebral implants are usually inserted between the adjacent vertebral body surfaces situated ventrally of the vertebral canal and so it is customary to effect the insertion of such intervertebral implants from a ventral direction. Dorsal introduction presents serious problems.

Intervertebral implants are known, which may be introduced dorsolaterally into the intervertebral space; such a vertebral body is described, for example, in DE 297 20 022 U1. In said document, however, it is not specified how, given said complicated access, the intervertebral implant is to be introduced successfully in the correct position into the intervertebral space.

The object is therefore to provide a surgical instrument, which facilitates the introduction of an intervertebral implant into the intervertebral space, especially in the case of dorsolateral introduction.

In a surgical instrument of the type described initially, said object is achieved according to the invention in that it comprises two mutually opposing guide bodies, which each have a guide directed towards the other guide body and together form between them a guideway, along which an intervertebral implant is insertable laterally into the intervertebral space.

Such an instrument may be conveyed with the two guide bodies through the body access and into the intervertebral space so that the free end of the guide bodies extends into the intervertebral space. An intervertebral implant to be inserted into the intervertebral space may then be fed forward along the guideway thus formed until the intervertebral implant passes laterally into the intervertebral space and, there, assumes the desired position exclusively through being fed forward along the guideway.

In said case, it is advantageous when the guideway in the plane of displacement extends in the shape of an arc so that the implant at the start of the guideway is introduced obliquely into the body and may then pass exactly transversely into the intervertebral space.

In a particularly preferred form of construction it is provided that the space between the guide bodies is open at least at one side along the guideway. It is therefore possible to feed the intervertebral implant forward along the guideway by means of a forward feed instrument, wherein the forward feed instrument passes through the space between the guide bodies.

It may further be provided that the guide bodies at their free end carry extensions, which are placeable against the vertebral bodies forming the intervertebral space and which are disposed next to the guideway in such a way that the intervertebral implant, which is fed forward along the guideway, at the end of the guideway next to the extension is placeable against the adjacent vertebral bodies. The extensions therefore position the guide bodies at the vertebral bodies forming the intervertebral space but are not situated in the guideway of the intervertebral implant, with the result that the latter in the course of forward feeding along the guideway lies at the end of the guideway next to said extensions and hence may leave the guideway and place itself directly against the adjacent vertebral bodies.

In particular, the extensions may take the form of prongs projecting pairwise in the direction of displacement from the end of the guideway in continuation thereof.

In a particularly preferred form of construction it is provided that the guide bodies are adjustable in terms of their mutual spacing. Thus, it is possible by means of the guide bodies, which at their free end rest against the adjacent vertebral bodies, also to spread the vertebral bodies apart so as to gain access to the intervertebral space. The guide bodies therefore perform a dual function, namely, on the one hand, the function of spreading the intervertebral space and, on the other hand, the function of guiding the intervertebral implant into the intervertebral space.

In particular, the guideway may be designed in such a way that an intervertebral implant conveyed between the guide bodies is guided in the guideway even when the distance between the guide bodies increases.

A particularly advantageous form of construction arises when the guide bodies at their opposite end to the free end are pivotally connected to one another so that a swivelling-open of the guide bodies then leads simultaneously to the spreading-apart of the vertebral bodies in the region of the intervertebral space.

In a special form of construction it is provided that each guide body comprises a flat bearing surface for the intervertebral implant and said bearing surface has laterally delimiting walls, which extend parallel to one another along the guide body and project in the direction of the other guide body beyond the bearing surface. The guideway is therefore formed by two guide bodies, which are U-shaped in cross section and surround the intervertebral implant at the top and underside and partially at the side surfaces.

It is advantageous when the guideway at its opposite end to the free end of the guide bodies exits laterally from the instrument so that an intervertebral implant is insertable into the guideway there.

In a particularly preferred form of construction it is provided that between the two guide bodies along the guideway formed by the latter a forward feed body is displaceably supported, which comprises a releasable holding device for the intervertebral implant. In said form of construction, therefore, a slide-like guide body is formed on the guideway as a driver for the intervertebral implant.

In said case, it is advantageous when the forward feed body comprises a receiving space, which is open towards the—in forward feed direction—front end of the forward feed body, for the intervertebral implant. The latter is accommodated in said receiving space, fed in said arrangement together with the forward feed body forward along the guideway and then, by retracting the forward feed body, released from the receiving space through the open side of the latter.

The receiving space may preferably be delimited by two side walls, which extend along the guideway.

In particular, it may be provided that the releasable holding device comprises elastic detent devices, which spring into recesses. The intervertebral implant is therefore held in the receiving space by a snap or detent connection, which may be released by pulling the intervertebral implant vigorously out of the receiving space.

The forward feed body at its—in forward feed direction—rear end may comprise an access opening for a retaining element placeable on the intervertebral implant so that, after inserting the intervertebral implant, the latter may be retained in the attained position between the vertebral bodies by the retaining element when the forward feed body is retracted. In said case, the intervertebral implant exits from the receiving space of the forward feed body.

In particular, the retaining element may be curved in accordance with the guideway.

In a preferred form of construction it is provided that the forward feed body is connected to a curved forward feed rod, which is displaceable along the guideway. The connection between forward feed body and forward feed rod may in said case be releasable.

It is particularly advantageous when the forward feed rod takes the form of a toothed rack, which meshes with a toothed wheel rotatably supported on a guide body. By turning the toothed wheel the surgeon may therefore displace the forward feed rod, and hence the forward feed body and the intervertebral implant held thereon, along the guideway.

The forward feed rod may comprise a longitudinal groove for receiving and guiding a retaining element for the intervertebral implant.

In a particularly preferred form of construction it is provided that the guide bodies from their swivel bearing point up to their free end are at a decreasing distance from one another, which at the—in forward feed direction—rear insertion end of the guideway is greater than the height of the intervertebral implant and optionally the height of the forward feed body but at the—in forward feed direction—front outlet end of the guideway is smaller than the height of the intervertebral implant and/or of the forward feed body. Thus, the forward feed body and/or the intervertebral implant in the course of being fed forward along the guideway act as spreading bodies, which swivel the two guide bodies apart and hence increase the distance between the two vertebral bodies, between which the free end of the guide bodies is inserted and between which the intervertebral implant is to be inserted. The forward feed motion itself therefore leads to the spreading of the intervertebral space so that the surgeon does not simultaneously have to effect the spreading and check the forward feed along the guideway, rather the surgeon merely has to feed the intervertebral implant forward along the forward feed path and the required distance between the adjacent vertebral bodies for introduction of the intervertebral implant then arises automatically.

In said case, it is advantageous when the forward feed body and/or the guide bodies at the surfaces, which are in mutual contact, are made of a low-friction material, e.g. the appropriate surfaces may be coated with a slidable plastics material.

In another form of construction of the invention it is provided that both guide bodies are firmly connected to gripping branches, which extend beyond the hinged connecting point of the guide bodies. The end result is a forceps-like instrument, in which by pressing the gripping branches towards one another the guide bodies are swivelled apart.

It is advantageous when a stop for maintaining a minimum distance between the two guide bodies is disposed on the instrument, thereby ruling out the possibility of the intervertebral implant becoming jammed along its guideway.

The stop may preferably be adjustable so that the minimum distance may be adapted to the size of the respective implant.

Figure 2:
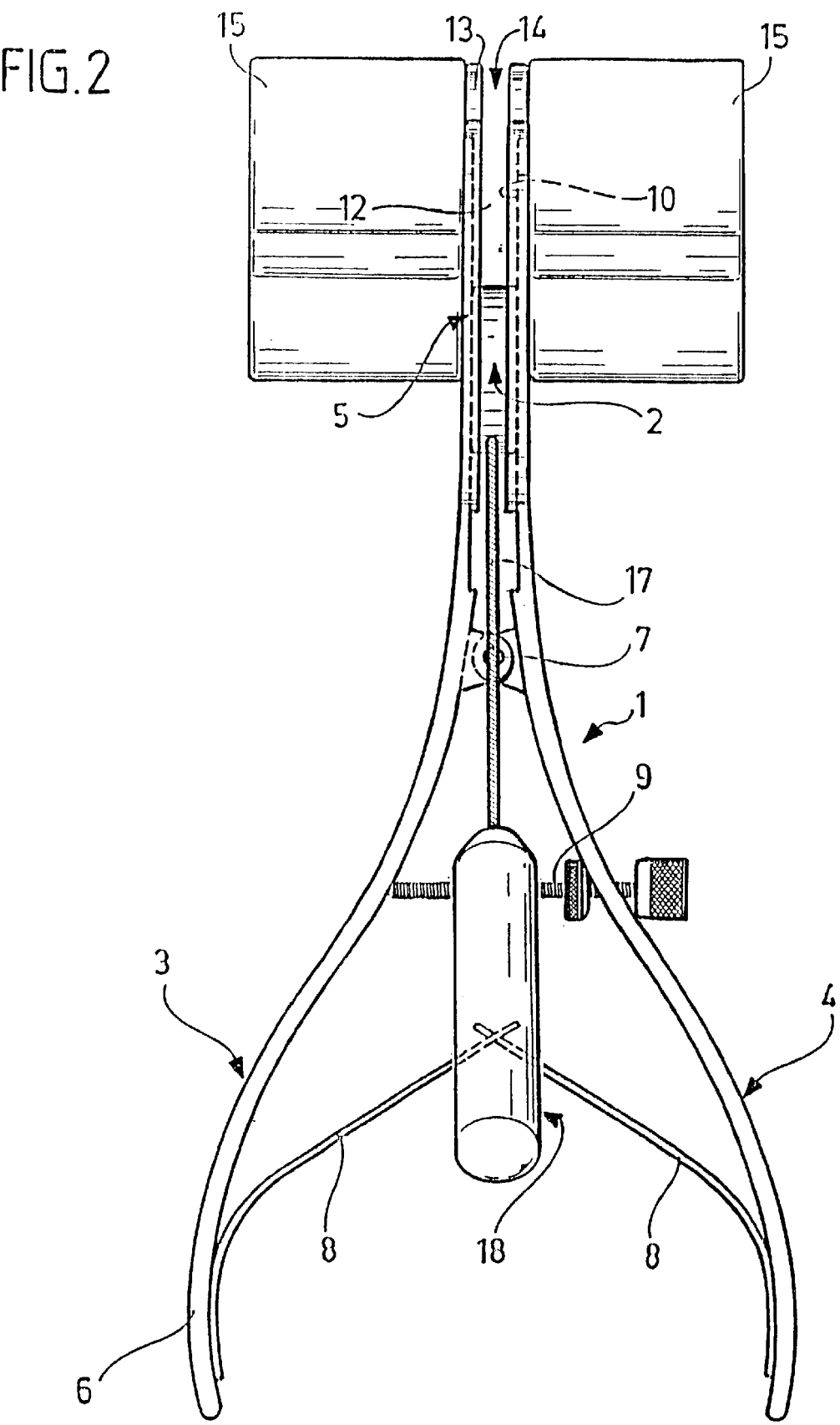
Figure 3:
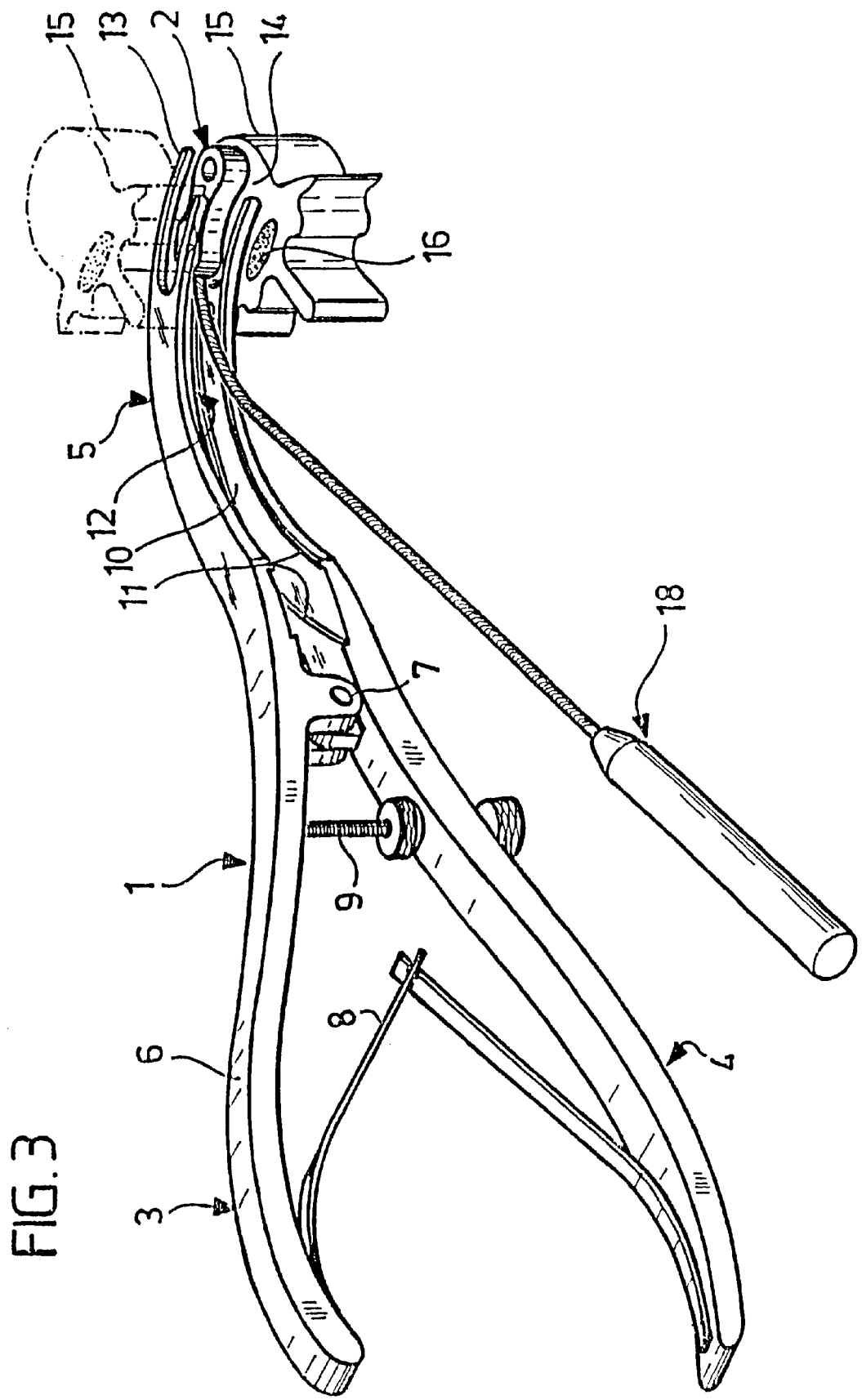
Figure 9:
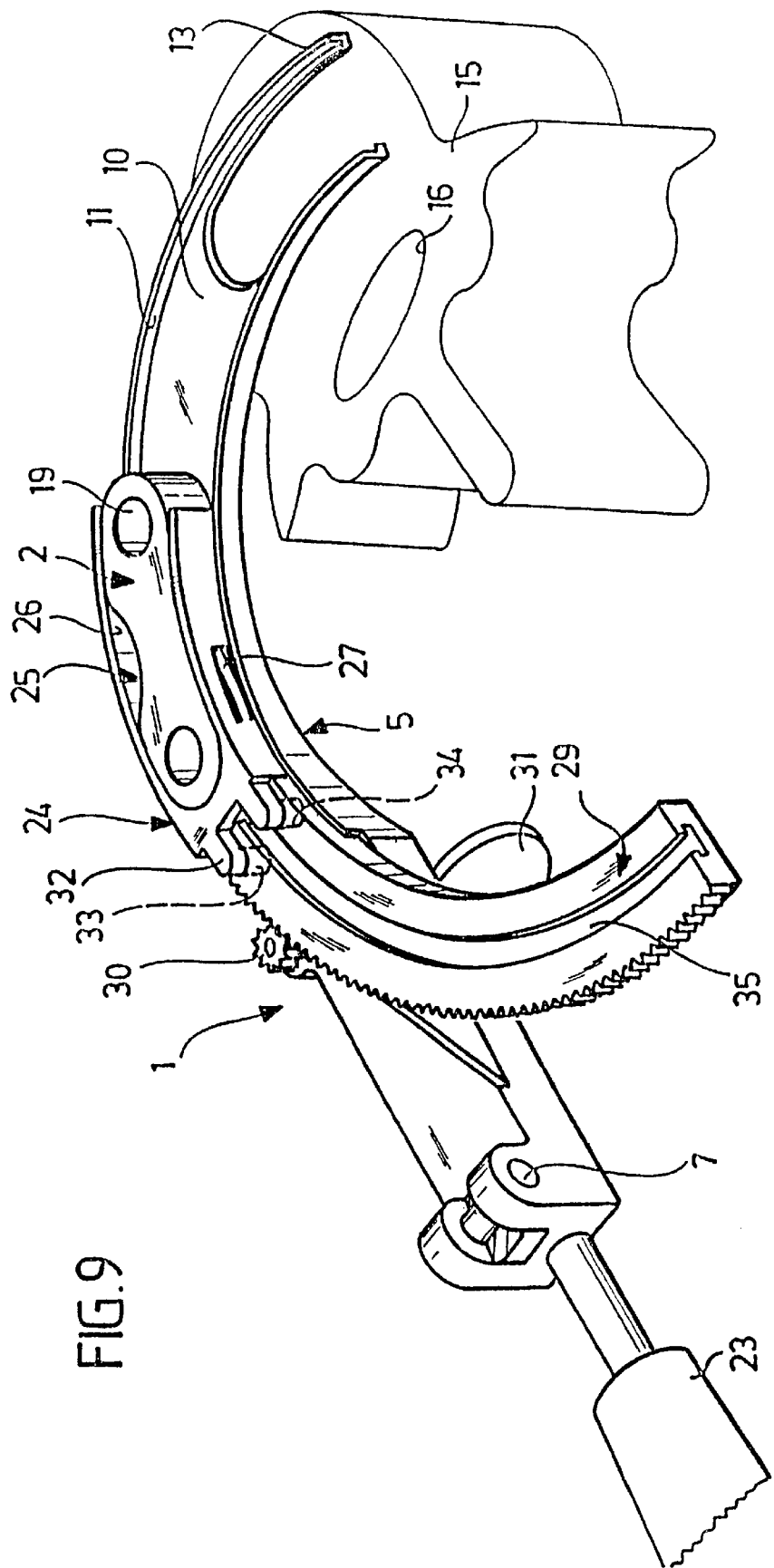
Figure 10:
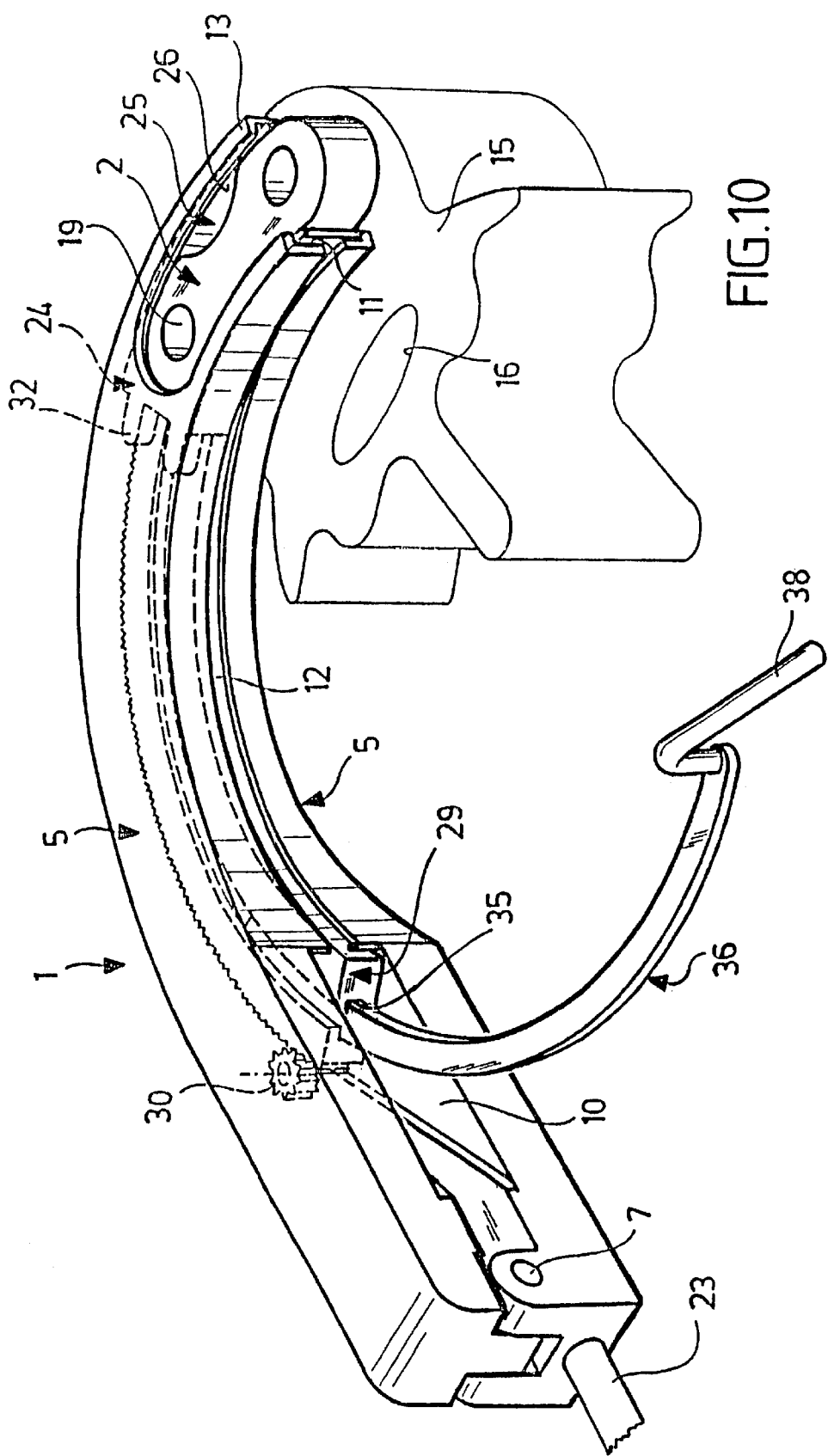
Figure 11:
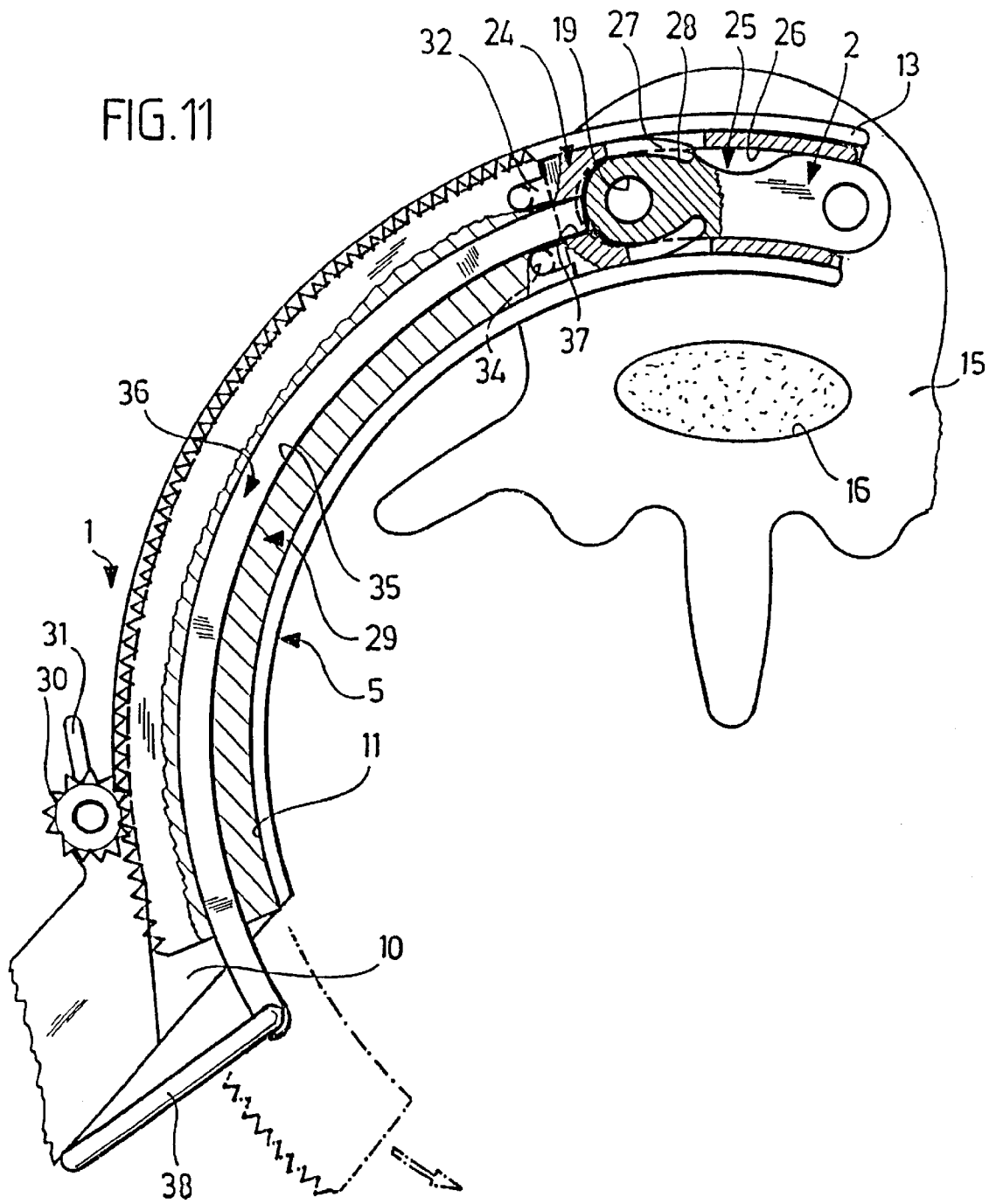

There now follows a detailed description of preferred forms of construction of the invention with reference to the drawings. The drawings show:

FIG. 1: a plan view of a surgical guiding and spreading instrument with an intervertebral implant being fed forward along the guideway by means of an insertion instrument;

FIG. 2: a side view in the direction of the arrow A in FIG. 1;

FIG. 3: a perspective view of the surgical instrument inserted into the intervertebral space and with the intervertebral implant in the end position in the intervertebral space;

FIG. 4: a perspective view of an intervertebral implant in the intervertebral space with an inserted apparatus for introducing bone material;

FIG. 5: a plan view of a first preferred embodiment of an intervertebral implant with curved longitudinal sides at the end of the surgical insertion instrument;

FIG. 6: a view similar to FIG. 5 having two intervertebral implants inserted adjacent to one another at the end of the surgical insertion element;

FIG. 7: a view similar to FIG. 6 in the case of intervertebral implants having a rectangular cross section;

FIG. 8: a plan view of a further preferred form of construction of a surgical guiding and spreading instrument with the top guide body removed;

FIG. 9: a perspective view of the instrument of FIG. 8 with the top guide body removed;

FIG. 10: a view similar to FIG. 9 with mounted top guide body and inserted retaining element, and FIG. 11: a view similar to FIG. 8 with fully inserted forward feed body and fully inserted retaining element.

The instrument 1 shown in FIGS. 1 to 3 for introducing an intervertebral implant 2 is designed in the manner of forceps and comprises two arms 3, 4, which are substantially identical in construction. Each arm comprises a flat guide body 5 and an adjoining gripping part 6 extending laterally out of the plane of the guide body 5, both arms 3, 4 are pivotally connected to one another in the transition region between the guide bodies 5 and the gripping parts 6 by a hinge 7 in such a way that, when the gripping parts 6 are pressed towards one another, the guide bodies 5 are swivelled apart from one another.

Disposed between the gripping parts 6 are spring elements 8, which spread the gripping parts 6 apart from one another, and one of the gripping parts 6 is penetrated by a spindle 9, which may be screwed in to a greater or lesser degree in the direction of the other gripping part 6 and forms a stop, by means of which the approach of the two gripping parts 6 may be limited.

The two guide bodies 5 are U-shaped in cross section and comprise a mutually opposing flat guide surface 10 laterally delimited by side walls 11, which extend over the entire length of the guide surface 10, project in the direction of the other guide body and also, when the guide bodies 5 have approached one another to the maximum extent, between them maintain a slot-shaped space 12 (FIG. 2). The two guide bodies 5 therefore form between them a guideway, which is delimited at the top and at the underside by the two guide surfaces 10 and at the sides by the side walls 11.

The guide bodies 5 are of a curved design in the plane defined by the guide surface 10, e.g. said curve extends over an angle of 90°, so that the guideway is also curved (FIG. 1). In said case, the guideway at its end lying near the hinge 7 may exit laterally from the guide bodies 5 so that, at said point, an intervertebral implant 2 may be inserted into the guideway (FIG. 1).

At the free end of the guide surfaces 10 the side walls 11 continue further in extension of the guide surfaces 10 and therefore form extensions 13, which extend pairwise alongside one another and might also be described as prongs.

As a result, there is still lateral guidance of intervertebral implants fed forward along the guideway; since the guide surfaces 10 however terminate sooner and there is no longer guidance in an upward and downward direction, in the region between the extensions 13 windows are practically formed, through which implants fed forward along the guideway and up to the end thereof may exit in an upward or downward direction from the guideway.

To insert an intervertebral implant 2, the described implant 1 with the guide bodies 5 is introduced through a body access as far as into the intervertebral space 14 between two adjacent vertebral bodies 15, namely in such a way that the prong-shaped extensions 13 pass laterally into the intervertebral space, and indeed directly adjacent to and ventrally of the vertebral canal 16. The guide surfaces 10 terminate in said case shortly before entry into the intervertebral space 14, while the prong-shaped extensions 13 extend fully into the intervertebral space 14.

After the extensions 13 have been introduced into the intervertebral space 14, the guide bodies 5 are spread apart by means of the gripping parts 6, thereby also increasing the distance between the vertebral bodies 15, i.e. widening the intervertebral space 14.

An intervertebral implant 2, which is to be inserted into the intervertebral space 14 and may, for example, take the form of an elongate plate, is then inserted along the guideway formed by the guide bodies 5 and into the intervertebral space 14.

To said end, the plate-shaped intervertebral implant 2 is connected to the thin flexible shank 17 of an insertion instrument 18, e.g. by screwing the flexible shank 17 into an internal thread of the intervertebral implant.

By means of said insertion instrument 18 the intervertebral implant 2 is displaced along the guideway until it is situated in the intervertebral space 14 between the prong-shaped extensions 13 and hence has reached the end of the guideway. Forward feeding is easily possible because the adjacent vertebral bodies 15 are held an adequate distance apart by the guide bodies 5.

As soon as the intervertebral implant 2 has reached its position between the prong-shaped extensions 13, it falls out of the guideway formed by the guide bodies 5 and places itself against the adjacent vertebral bodies. The surgeon may then ease off the pressure on the gripping parts 6 of the instrument 1 and hence end the spreading of the intervertebral space 14 so that the vertebral bodies 15 move towards one another and come to rest against the intervertebral implant 2 on both sides. The instrument 1 may then be withdrawn without difficulty from the intervertebral space 14 and from the body.

During insertion of the implant it is advantageous that the shank 17 of the insertion instrument 18 need not necessarily be disposed along the guideway but may exit laterally from the guideway since the shank 17 passes through the space 12 between the guide bodies 5.

As soon as the intervertebral implant 2 has been inserted in the described manner into the intervertebral space 14, the insertion instrument 18 may also be removed, e.g. by screwing the shank 17 out of the screw-in thread.

Through suitable introduction channels in the intervertebral implant 2 bone material may be introduced into the part of the intervertebral space 14 not filled by the intervertebral implant 2 and, optionally, into holes 19 in the intervertebral implant 2. This may be effected with the aid of a filling instrument 20, which comprises a filling tube 21, into which bone material may be introduced. By means of a plunger 22 the bone material may be pushed out of the filling tube 21 at the free end thereof. When the free end of said filling tube 21 is applied to the described introduction channel of the intervertebral implant 2, bone material passes through said introduction channel and into the holes 19 of the intervertebral implant 2 and through the entire intervertebral implant 2 into the part of the intervertebral space 14 disposed ventrally of the intervertebral implant 2, so that a bed of bony substance is formed very effectively around the intervertebral implant 2.

The shape of the intervertebral implant 2 may in said case differ widely. In the embodiments of FIGS. 1 to 3 an intervertebral implant 2 is shown, which is elongate and slightly curved and is narrower in the middle region than in the end region. In said middle region the implant is recessed at its ventral longitudinal side so as to form there a receiving space for bone material which, once the intervertebral implant 2 is inserted, leads to a positive embedding of the intervertebral implant 2 in the intervertebral space 14.

A similarly shaped implant without such recessing is shown in FIG. 5.

In the embodiment of FIG. 6, instead of one intervertebral implant 2 two intervertebral implants 2 are inserted at a distance from one another, said insertion being effected in successive insertion operations exactly in the same manner as has been described for the implant of FIGS. 1 to 3. The implants 2 of FIG. 6 have a substantially oval or elliptical cross section, in the embodiment of FIG. 7 two implants having a substantially rectangular cross section are provided, which are also inserted in a similar manner.

FIGS. 8 to 11 show a further preferred embodiment of an instrument 1, which is of a similar construction to the instrument of FIGS. 1 to 3, for which reason parts corresponding to one another bear the same reference characters.

In said embodiment, unlike the embodiment of FIGS. 1 to 3, the guide bodies are not provided with branch-like gripping parts 6 and so the instrument does not have the configuration of forceps. Rather, the two guide bodies 5 are connected to one another likewise via a hinge 7 and terminate at said hinge 7, wherein one of the two guide bodies 5 in said case carries a handle 23. Alternatively, it might be provided that one of the two branch-like gripping parts 6 in the region of the hinge 7 is of a removable design and the remaining gripping part is used as a handle.

Given such a construction of the instrument, the spreading is effected not by pressing branch-like gripping parts together but exclusively in that the parts, which are fed forward along the guideway, in the course of forward feeding push the guide bodies 5 apart from one another and so the free ends of the latter, which engage between the vertebral bodies 15, increase the distance between the vertebral bodies 15. To said end, the guide bodies 5 are designed in such a way that at the insertion end they are at a distance from one another, which is greater than the height of the parts fed forward between the guide bodies 5, but at the outlet end of the guide bodies 5 are a smaller distance apart. Thus, the unspread guide bodies 5 may pass with their free end into the unwidened intervertebral space, the parts fed forward between the guide bodies may easily be inserted at the insertion end, and it is only by virtue of the forward feed motion of the forward fed parts itself that the spreading-apart of the guide bodies 5 and hence the widening of the intervertebral space 14 is effected.

The parts fed forward between the guide bodies 5 may be formed quite simply by the intervertebral implant 2 itself, although it is advantageous when—as shown in the embodiment of FIGS. 8 to 11—between the guide bodies 5 a special forward feed body 24 is supported so as to be displaceable along the guideway, which forward feed body rests against the two guide bodies 5 and effects said spreading. The forward feed body 24 is of an elongate design and rests on both sides against the side walls 11 of the guide bodies 5 so that it is guided precisely along the guideway. It comprises an elongate receiving space 25, which is formed by the side walls 26 of the forward feed body 24, which extend substantially parallel to one another, and is open at the top and at the underside as well as at the—in forward feed direction—front end. The intervertebral implant 2 is inserted from the open side into said receiving space 25 between the side walls 26 and is held in the inserted position by elastic detent tongues 27, which are incorporated in the side walls 26 of the forward feed body 24 and engage elastically into lateral recesses 28 of the intervertebral implant 2 (FIG. 11).

In the embodiment illustrated in the drawings, the height of the intervertebral implant 2 is equal to the height of the forward feed body 24, in which case intervertebral implant and forward feed body in the course of being fed forward along the guideway jointly spread the guide bodies 5 apart. The intervertebral implant might alternatively be of a slightly smaller height than the forward feed body, in which case the spreading would be effected exclusively by the forward feed body.

The forward feed body 24 is connected to a curved toothed rack 29, which is guided in one of the two guide bodies 5 and meshes with a toothed wheel 30, which is rotatably supported on one of the guide bodies 5 and is rotatable via a turning handle 31 so that the toothed rack 29 may be pushed forward and back along the guideway. Said connection between forward feed body 24 and toothed rack 29 is releasable, in the illustrated embodiment the forward feed body 24 carries on each of two projecting lugs 32 a vertically downward projecting pin 33, which is insertable into a bore 34 at the end of the toothed rack 29.

Disposed in the top of the toothed rack 29 is an upwardly open longitudinal central groove 35, in which a curved, rod-shaped retaining element 36 is feedable in forward direction. The front end of the longitudinal central groove 35 communicates with an opening 37 in the forward feed body 24, through which opening 37 the retaining element 36 may be fed forward into the receiving space 25 and, there, apply itself against the intervertebral implant 2 held in the receiving space 25 (FIG. 11).

To insert the intervertebral implant 2, the latter is pushed into the receiving space 25 until the detent tongues 27 snap into the recesses 28. The forward feed body 24 may then be pushed in at the insertion end between the guide bodies 5 and connected to the toothed rack 29, which is likewise partially inserted between the guide bodies, by inserting the pins 33 into the bores 34.

Said insertion of the forward feed body 24 and of the toothed rack 28 may already be effected prior to insertion of the instrument into the body but it will be advantageous first to introduce the empty instrument 1 into the body until the free end of the guide bodies passes into the intervertebral space 14, into which the intervertebral implant 2 is to be inserted.

By turning the toothed wheel 30 the toothed rack 29 is fed forward between the guide bodies and therefore gradually feeds the forward feed body 24 with the intervertebral implant 2 forward into the intervertebral space 14, which is widened as a result of the guide bodies 5 being spread in the course of said forward feed motion.

As soon as the intervertebral implant 2 is situated in the end position in the intervertebral space 14, the retaining element 36 is inserted until it comes to rest against the intervertebral implant 2. The depth of insertion of the retaining element 36 may in said case be limited by a stop formed, for example, by a laterally bent portion 38 of the retaining element 36 which comes into abutment with the guide body 5 (FIG. 11). When the forward feed body 24 and the toothed rack 29 are retracted, the elastic detent connection between the detent tongues 27 and the recesses 28 is thereby released because the intervertebral implant 2 is retained in the intervertebral space 14 by the retaining element 36. To said end, the retaining element 36 is detachably fastenable to the guide body 5 by means not illustrated in the drawing. In said manner, forward feed body 24, toothed rack 29 and subsequently also the retaining element 36 may be withdrawn from the instrument 1, wherein the spreading of the vertebral bodies 15, which delimit the intervertebral space 14, is cancelled, the vertebral bodies 15 are then supported on the intervertebral implant 2 and the instrument may then be withdrawn entirely from the intervertebral space 14.

What is claimed is:

1. Surgical instrument for introducing intervertebral implants into the intervertebral space between adjacent vertebral bodies, comprising:
   two mutually opposing guide bodies, which each have a guide directed towards the other guide body and together form between them a guideway, along which an intervertebral implant is insertable laterally into the intervertebral space,
   wherein:
   the guide bodies are adjustable in terms of their mutual distance; and
   the guideway in the plane of displacement extends in the shape of an arc.

2. Surgical instrument according to claim 1, wherein a space between the guide bodies is open at least at one side along the guideway.

3. Surgical instrument according to claim 1, wherein the guide bodies have a free end and, there, carry extensions, which are placeable against vertebral bodies forming the intervertebral space and which are disposed next to the guideway in such a way that the intervertebral implant, which is fed forward along the guideway, at an end of the guideway next to the extension is placeable against the adjacent vertebral bodies.

4. Surgical instrument according to claim 3, wherein the extensions take the form of prongs projecting pairwise in the direction of displacement from the end of the guideway in continuation thereof.

5. Surgical instrument according to claim 1, wherein the guideway is delimited at a top and at an underside by two guide surfaces and at the sides by side walls, which between them maintain a slot-shaped space so that an intervertebral implant conveyed between the guide bodies is guided in the guideway even when the distance between the guide bodies increases.

6. Surgical instrument according to claim 1, wherein the guide bodies have a free end and are pivotally connected to one another at an opposite end to the free end.

7. Surgical instrument according to claim 6, wherein each guide body comprises a flat bearing surface for the intervertebral implant and said bearing surface has laterally delimiting guide walls, which extend parallel to one another along the guide body and project in the direction of the other guide body beyond the bearing surface.

8. Surgical instrument according to claim 6, wherein both guide bodies are firmly connected to gripping branches, which extend beyond a hinged connecting point of the guide bodies.

9. Surgical instrument according to claim 6, an intervertebral implant insertable through said instrument into an intervertebral space, wherein the guide bodies from a swivel bearing point up to their free end are at a decreasing distance from one another, which at a rear insertion end of the guideway is greater than the height of the intervertebral implant and optionally of the forward feed body but at a front outlet end of the guideway is smaller than at least one of the height of the intervertebral implant or of the forward feed body.

10. Surgical instrument according to claim 9, wherein at least one of the forward feed body or the guide bodies at the surfaces, which are in mutual contact, are made of a low-friction material.

11. Surgical instrument according to claim 1, wherein each guide body comprises a flat bearing surface for the intervertebral implant and said bearing surface has laterally delimiting guide walls, which extend parallel to one another along the guide body and project in the direction of the other guide body beyond the bearing surface.

12. Surgical instrument according to claim 1, wherein the guide bodies have a free end and the guideway at an opposite end to the free end of the guide bodies exits laterally from the instrument so that an intervertebral implant is insertable into the guideway there.

13. Surgical instrument according to claim 1, further comprising a stop for maintaining a minimum distance between the two guide bodies.

14. Surgical instrument according to claim 13, wherein the stop is adjustable.

15. Surgical instrument according to claim 1, wherein supported between the two guide bodies so as to be displaceable along the guideway formed by the guide bodies is a forward feed body, which comprises a releasable holding device for the intervertebral implant.

16. Surgical instrument according to claim 15, wherein the forward feed body comprises a receiving space, which is open towards a front end of said forward feed body, for receiving the intervertebral implant.

17. Surgical instrument according to claim 16, wherein the receiving space is delimited by two side walls, which extend along the guideway.

18. Surgical instrument according to claim 16, wherein the forward feed body at its rear end has access opening for a retaining element, which is placeable against the intervertebral implant.

19. Surgical instrument according to claim 18, wherein the retaining element is curved in accordance with the guideway.

20. Surgical instrument according to claim 15, wherein the releasable holding device comprises elastic detent devices, which spring into recesses.

21. Surgical instrument according to claim 15, wherein the forward feed body is connected to a curved forward feed rod, which is displaceable along the guideway.

22. Surgical instrument according to claim 21, wherein the forward feed body and forward feed rod are releasibly connected.

23. Surgical instrument according to claim 21, wherein the forward feed rod takes the form of a toothed rack, which meshes with a toothed wheel rotatably supported on a guide body.

24. Surgical instrument according to claim 21, wherein the forward feed rod comprises a longitudinal groove for receiving and guiding a retaining element for the intervertebral implant.

* * * * *